United States Patent [19]

Sato et al.

[11] Patent Number: 5,583,158
[45] Date of Patent: Dec. 10, 1996

[54] PROSTAGLANDIN $E_1$ ANALOGUES

[75] Inventors: Fumie Sato, Fujisawa; Takehiro Amano, Tokyo; Kazuya Kameo, Tokyo; Tohru Tanami, Tokyo; Masaru Mutoh, Tokyo; Naoya Ono, Tokyo; Jun Goto, Tokyo, all of Japan

[73] Assignee: Taisho Pharmaceutical Co., Ltd., Japan

[21] Appl. No.: 416,871

[22] PCT Filed: Oct. 20, 1993

[86] PCT No.: PCT/JP93/01510

§ 371 Date: Apr. 19, 1995

§ 102(e) Date: Apr. 19, 1995

[87] PCT Pub. No.: WO94/08961

PCT Pub. Date: Apr. 28, 1994

[30] Foreign Application Priority Data

Oct. 21, 1992 [JP] Japan ................................ 4-282088

[51] Int. Cl.⁶ ....................... A61K 31/557; C07C 405/00
[52] U.S. Cl. .................... 514/530; 514/573; 560/121; 562/503
[58] Field of Search ................. 560/121; 562/503; 514/530, 573

[56] References Cited

U.S. PATENT DOCUMENTS

| | | |
|---|---|---|
| 4,029,681 | 6/1977 | Smith . |
| 4,131,737 | 12/1978 | Floyd, Jr. et al. . |
| 4,131,738 | 12/1978 | Smith . |
| 5,449,815 | 9/1995 | Sato ........................ 560/121 |

FOREIGN PATENT DOCUMENTS

| | | |
|---|---|---|
| 100446 | 8/1977 | Japan . |
| 5439047 | 7/1978 | Japan . |
| 5446748 | 8/1978 | Japan . |
| 5117230 | 7/1991 | Japan . |
| 2006186 | 8/1978 | United Kingdom . |

OTHER PUBLICATIONS

J. Org. Chem., vol. 53, p. 5590 (1988) (p. 6 lines 19–20).
Tetrahedron Lett., vol. 30, p. 7083 (1989) (p. 6 line 36) (p. 7) (line 1).
Nature, vol. 194, p. 927 (1962) (p. 11, lines 31–32).
English Abstract for Japanese 5117230, (1991).

Primary Examiner—Robert Gerstl
Attorney, Agent, or Firm—Lorusso & Loud

[57] ABSTRACT

A prostaglandin $E_1$ analogue represented by formula

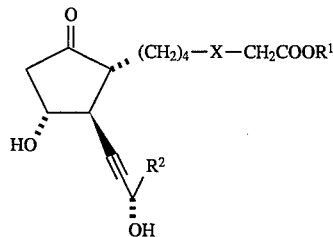

wherein $R^1$ represents a hydrogen atom or a $C_1$–$C_6$ alkyl group; and X is an oxygen atom and $R^2$ represents

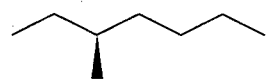

or

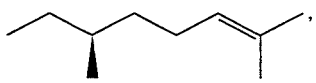

or X is a sulfur atom and $R^2$ represents

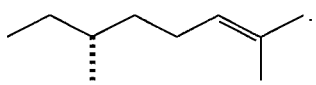

The compound has a strong and prolonged inhibitory action for platelet aggregation and is useful for treatment of various thrombotic diseases including peripheral circulatory disturbance.

4 Claims, No Drawings

PROSTAGLANDIN $E_1$ ANALOGUES

This application is a 371 of PCT/JP93/01510 filed Oct. 20, 1993.

TECHNICAL FIELD

The present invention relates to novel prosta-glandin $E_1$ analogues.

BACKGROUND ART

Since prostaglandin (hereinafter referred to as PG) shows various important physiological actions in a trace amount, natural PG analgogues and a vast number of derivatives thereof have been studied on synthesis and biological activities, with attempts to apply these compounds to pharmaceuticals. In particular, $PGE_1$ has characteristic actions such as platelet aggregation inhibition, blood pressure lowering and the like and is already inpractical use as a drug for ameliorating peripheral circulatory disturbance. Therefore, a large number of $PGE_1$ analogues have been investigated. Hitherto known $PGE_1$ anologues, however, have a drawback of quick metobolism in living body and consequent short term effect. Further, hitherto proposed $PGE_1$ analogues induce diarrhea as a side effect when administered orally and accordingly have a problem in that they cannot be administered orally in a sufficiently high amount to obtain the satisfactory effects.

Meanwhile, 13,14-didehydro-$PGE_1$ methyl ester and 6-hydroxy-13,14-didehydro-$PGE_1$ are known as 13,14-didehydro-$PGE_1$ analogues obtained by converting the double bond between the 13- and 14-positions of $PGE_1$ to a triple bond [Japanese Patent Application Kokai (Laid-Open) No. 100446/1977 and U.S. Pat. No. 4,131,738].

The main object of the present invention is to provide novel $PGE_1$ analogues which have a higher efficacy, a more prolonged action and a lower side effect then hitherto known $PGE_1$ analogues.

Disclosure of the Invention

The present inventors made a study and found out that $PGE_1$ analogues having a triple bond between the 13- and 14-positions, a branch the 17-position and on oxygen or sulfur atom at the 3-position in pace of methylene have excellent and prolonged physiological activities and a low side effect. The finding has led to the completion of the present invention.

Thus, the present invention provides a prosta-glandin $E_1$ analogue represented by formula

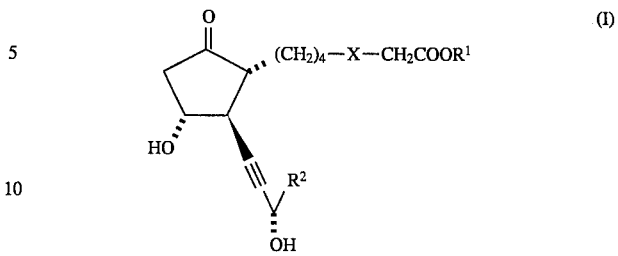

(I)

wherein $R^1$ represents a hydrogen atom or a $C_1$–$C_6$ alkyl group; and X is a oxygen atom and $R^2$ represents

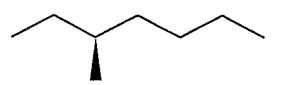

or

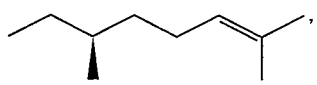

or X is a sulfur atom and $R^2$ represents

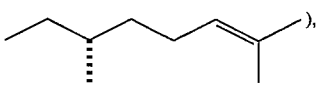

and a salt thereof.

In the present invention, "alkyl group" is a straight-chain or branched-chain saturated aliphatic hydrocarbon group. The $C_1$–$C_6$ alkyl group includes, for example, methyl, ethyl, n-propyl, isopropyl, n-butyl, isobutyl, sea-butyl, tert-butyl, n-pentyl, isopentyl and n-hexyl groups, etc. Of these, $C_1$–$C_4$ alkyl groups are preferable.

In the formula (I), $R^1$ is preferably a hydrogen atom or a $C_1$–$C_4$ alkyl group (a methyl group, in particular).

The compound of formula (T) wherein $R^1$ represents a hydrogen atom, can be present in the form of a free acid, or in the form of a salt. Examples of such salt include alkali metal salts such as sodium salt, potassium salt and the alkaline earth metal salts such as calcium salt, magnesium salt and the like; other metal salts such as aluminum salt and the like; ammonium salt; salts with organic amines such as trialkylamine (e.g. triethylamine), pyridine and the like. A pharmaceutically acceptable salt is particularly preferable.

The present compound of formula (I) can be produced, for example, by a process summarized in the following reaction scheme A.

Reaction Scheme A

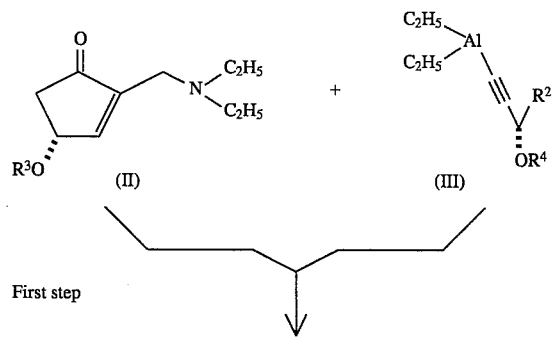

First step

-continued
Reaction Scheme A
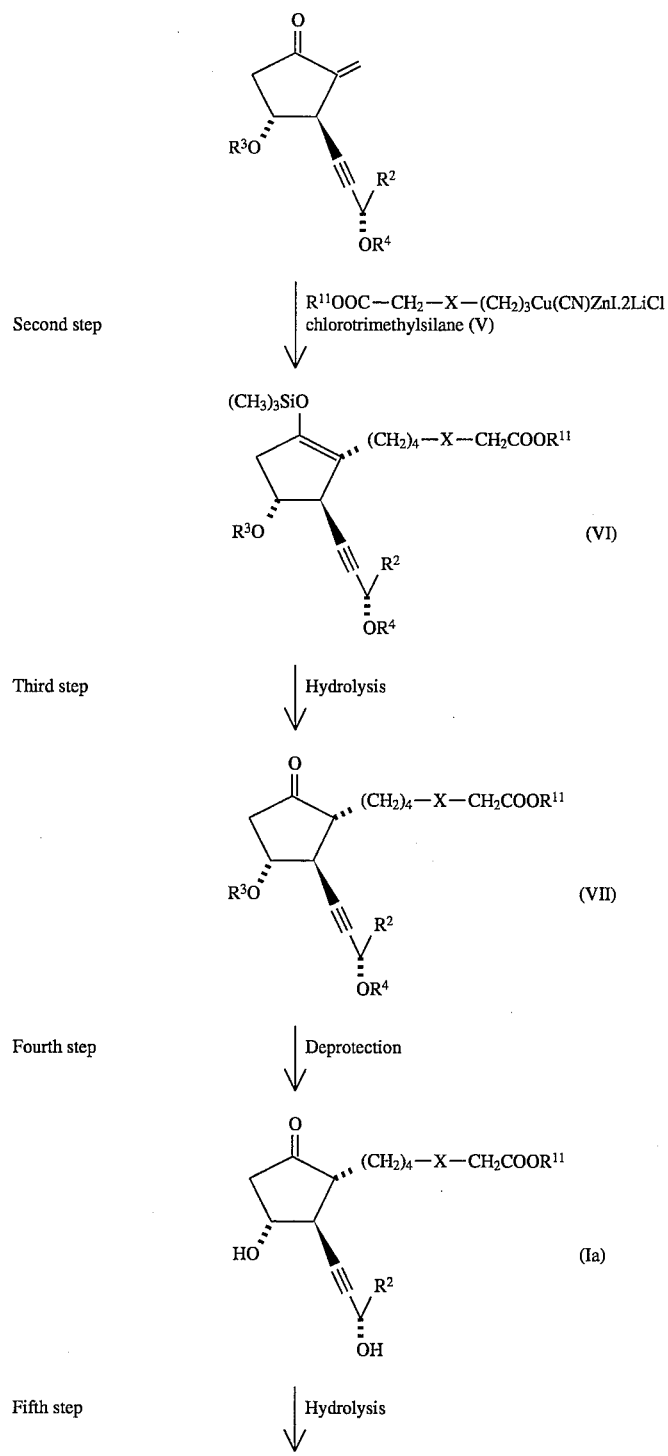
Second step
Third step  Hydrolysis
Fourth step  Deprotection
Fifth step  Hydrolysis -continued
Reaction Scheme A

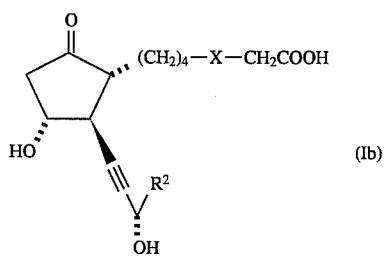

(Ib)

In the above reaction scheme, $R^{11}$ represents $C_1$–$C_6$ alkyl group; $R^3$ and $R^4$ which may be the same or different, each represent a protective group for hydroxyl group; and X and $R^2$ have the same definitions as given above.

The protective group for hydroxyl group can be a protective group which is removable by on ordinary reaction for protective group removal, such as hydrolysis, hydrocracking and the like and which is ordinarily used in prostaglandin chemistry. It includes, for example, tert-butyldimethylsilyl, triethylsilyl, phenyldimethylsilyl, tetrahydropyronyl, tetrahydrofuronyl, methoxymethyl, ethoxyethyl and benzyl groups, etc.

Each of the first to fifth steps is hereinafter described in more detail.

(First step)

First, a compound of formula (II) known via the process of Sato et al. [J. Org. Chem., Vol. 53, p. 5590 (1988)] is reacted with about 0.8- about 2 equivalents of an organoaluminum compound represented by formula (III) at a temperature of about −10° to about 30° C., preferably about 0° to about 10° C. in an inert solvent (e.g. benzene, toluene, tetrahydrofuron, diethyl ether, methylene chloride, n-hexane or the like) to obtain a compound of formula (IV) stereospecifically.

The organoaluminum compound of formula (III) used in the above reaction can be produced, for example, by mixing acetylene compound represented by formula

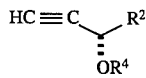

wherein $R^2$ and $R^4$ have the same definitions as given above), produced by the process of Sato et al. [Tetrahedron Lett., Vol. 30, p. 7083 (1989)] with about 0.8- about 1.5 equivalents of alkyllithium (e.g. n-butyllithium, tert-butyllithium or the like) at about −20° to about 30° C., preferably about −10° to about 0° C., preferably completing a reaction at about 10° to about 30° C., and then adding about 0.8- about 1.5 equivalents of diethylaluminum chloride at a temperature of about −20° to 300° C. In is generally preferable that this reaction is conducted in an inert organic solvent (e.g. benzene, toluene, tetrahydrofuron, diethyl ether, methylene chloride, n-hexane, or the like).

(Second step)

The compound of formula (IV) obtained in the first step is reacted with about 0.5- about 4 equivalents of on orgonocopper compound rerepresented by formula (V) and about 0.5- about 4 equivalents of chlorotrimethylsilane in an inert solvent (e.g. tetrahydrofuron, diethyl ether, methylene chloride, toluene, n-hexane or the like) at a temperature of about −78° to about 40° C. to form a compound of formula (VI).

The orgonocopper compound of formula (V) can easily be produced, for example, by a process shown by the following reaction scheme B.

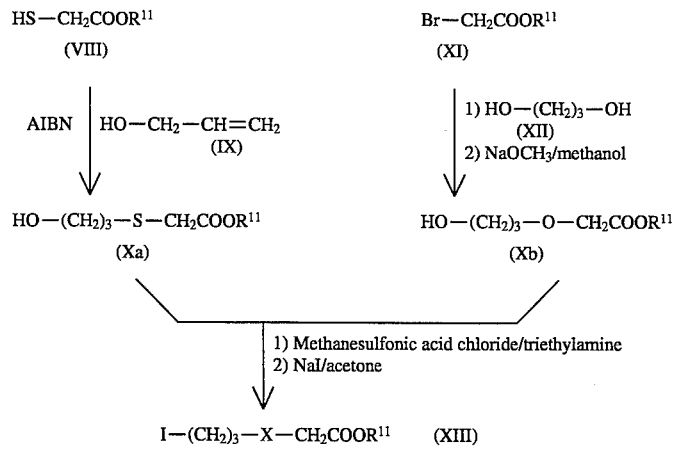

-continued
Reaction Scheme B

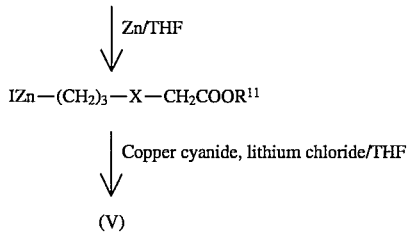

(V)

In the above reaction scheme, $R^{11}$ and X have the same definitions as given above.

A mercaptoacetic acid ester compound of formula (VIII) is reacted with an alcohol compound of formula (IX) and 2,2'-azobis(2-methylpropionitrile) (AIBN) to obtain a compound of formula (Xa). Separately, a bromoacetic acid ester of formula (XI) is reacted with an alcohol compound of formula (XII) and sodium hydride, followed by treatment with sodium methoxide in methenol, to obtain a compound of formula (Xb).

The compound of formula (Xa) and the compound of formula (Xb) are reacted in the presence of methanesulfonic acid chloride and triethylamine, followed by reaction with sodium iodide in acetone, to obtain a compound of formula (XIII).

The compound of formula (XIII) is reacted with about 0.8- about 5 equivalents of zinc a activated with, for example, 1,2-dibromomethane, chlorotrimethylsilane, iodine or the like, in an inert solvent (e.g. tetrahydrofuran, diethyl ether, n-hexane, n-pentane, dioxane or the like), whereby the compound of formula (XIII) can be converted into on organozinc a compound of formula (XIV). At this time, heating may be conducted as necessary. The temperature of heating varies depending upon the boiling point of the solvent used, but can be generally about 30° to about 150° C., preferably about 40° to about 80° C.

The organozinc compound of formula (XIV) is reacted in the same inert solvent as mentioned above, containing copper cyanide (about 1- about 2.5 equivalents) and lithium chloride (about 2- about 5 equivalents), whereby on organocopper compound of formula (V) can be obtained.
(Third step)

The compound of formula (VI) obtained in the second step is hydrolyzed by the use of an inorganic acid (e.g. an aqueous hydrochloric acid solution) or an organic acid or its amine salt (e.g. p-toluenesulfonic acid, pyridinium p-toluenesulfonate or the like) in an organic solvent (e.g. acetone, methenol, ethenol, isoproponol, diethyl ether, a mixed solvent thereof or the like) at a temperature of about 0° to about 40° C., whereby a compound of formula (VII) can be obtained stereoselectively.
(Fourth step)

The protective group for hydroxyl group, of the compound of formula (VII) obtained in the third step is deprotected by a method ordinarily used in prostaglandin chemistry, to obtain a compound of formula (I) of the present invention wherein $R^1$ is a $C_1-C_6$ alkyl group, i.e. a compound of formula (Ia).
(Fifth step)

The ester moiety ($R^{11}$) of the compound of formula (Ia) is hydrolyzed, whereby a compound of formula (I) of the present invention wherein is hydrogen atom, i.e. a compound of formula (Ib) can be obtained.

The hydrolysis can be conducted, for example, by reacting a compound of formula (Ia) with an enzyme in a buffer such as phosphate buffer, tris-hydrochloride buffer or the like with an organic solvent (miscible with water, such as acetone, methanol, ethanol or the like) used in combination as necessary. The enzyme usable includes, for example, hydrolases produced by microorganisims (e.g. enzymes produced by microorganisms belonging to Candida sp. and Pseudomonas sp.), hydrolases prepared from animal organs (e.g. enzymes prepared from pig liver and pig pan areas), etc. Specifiic examples of such an enzyme which is commeraically available, are Lipase VII (produced by Sigma Co.; derived from a microorganism of Candida sp.), Lipase AY (produced by Amano Pharmaceutical Co.; derived from a microorganism of Candida sp.), Lipase MF (produced by Amano Pharmaceutical Co.; derived from a microorganism of Pseudomonas sp.), PLE-A (produced by Amano Pharmaceutical Co.; prepared from pig liver), Esterase (produced by Sigma Co.; prepared from pig liver), Lipase II (produced by Sigma Co.; prepared from pig pancreas), Lipo-protein Lipase (produced by Tokyo Kasei Kogyo Co.; prepared from pig pancreas), etc.

The amount of the enzyme used can appropriately be determined depending upon the potency of the enzyme used and the amount of the substrate used [the compound of the formula (Ia)], but is generally about 0.1 to about 20 times (by weight) that of the substrate. The reaction temperature is about 25° to about 50° to C., preferably about 30° to about 35° C.

Each of the products obtained in the above steps can be, as necessary, separated from the reaction mixture and purified by a per se known method, for example, by chromatography, etc.

The present compound of formula (I), as is clear from the following Test Example, has a strong and prolonged inhibitory action for platelet aggregation. Further, the present compound induces substantially no diarrhea (diarrhea is currently the biggest problem of PG) at a dose reliably showing pharmacological actions. Therefore, the present compound is useful as a drug for treating various diseases including peripheral circulatory disturbance.

Test Example [Test for inhibition of rabbit platelet aggregation]

New Zealand White-strain rabbits (groups of four rabbits each weighing 2.5–4.0 to kg) were tested. Blood was collected from the common carotid artery of the rabbits under on ether anesthesic, and mixed with 3.2to % sodium citrate in volume ratio of 9:1. The blood was centrifuged at 1,100 rpm for 15 minutes to give a platelet-rich plasma (PRP) as a supernatant.

Blood platelet aggregation was determined according to the method of Born [Nature, Vol. 194, p. 927 (1962)]. To 275 to µl of PRP was added 1 µl of a solution of various concentrations of a test compound dissolved in ethanol; the mixture was stirred at 1,000 rpm at 37° C. for 3 minutes; then, in this state, 25 µl of an aggregation-inducing agent

[adenosine diphosphate (ADP), final concentration: 5 μM] was added thereto to induce platelet aggregation; and by using an aggregometer, there was determined the maximum aggregation rate (the maximum change in light transmission within 5 minutes from the induction of platelet aggregation).

The aggregation inhibition rate of the test compound was calculated from the maximum aggregation rate in the presence test compound relative to the maximum aggregation rate when ethanol was used instead of the solution of the test compound; the $IC_{50}$ value of the test compound was determined from the concentration response curve. The results are shown in Table 1.

TABLE 1

| Test Compound | $IC_{50}$ (nM) |
| --- | --- |
| Compound 1 | 0.60 |
| Compound 2 | 0.66 |
| Compound 3 | 0.39 |
| Compound 4 | 0.26 |
| Compound 5 | 0.67 |
| Compound 6 | 1.27 |
| Control A | 42.07 |
| Control B | 133.6 |
| Control C | 910.6 |
| Control D | 1522 |

Incidentally, in the above table, the number of each compound corresponds to the number of each compound shown in Examples described later; and control A, control B, control C and control D are compounds having the following structures, respectively.

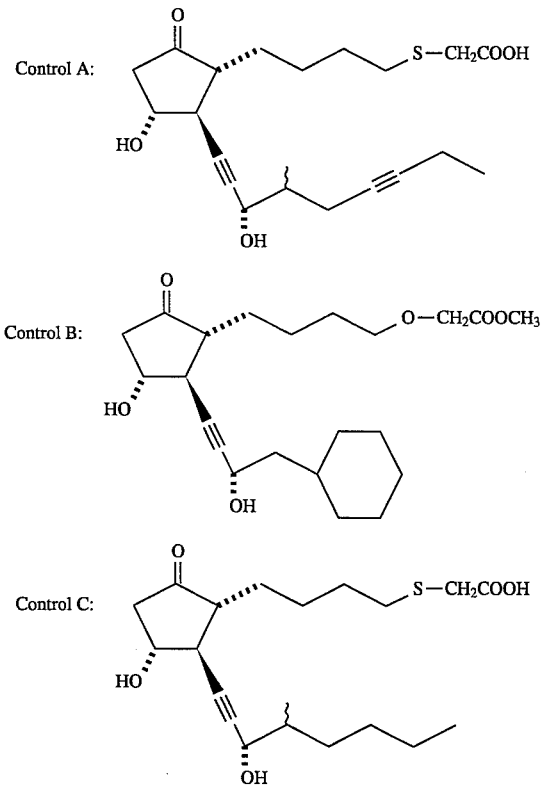

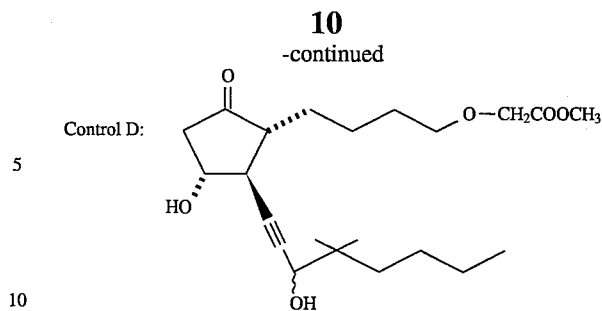

As described above, the compound of the present invention has a strong and prolonged inhibitory action for platelet aggregation. The present compound can therefore be administered to mammals, particularly humans as a drug for treating various thrombotic diseases including peripheral circulatory disturbance.

In order to use the compound of the present invention as a drug, the compound can be made into pharmaceutical preparations suitable for administration, together with pharmaceutically acceptable adjuvants and can be administered orally or parenterally (e.g. intravenously, intrarectally or intravaginally). As the preparation for oral administration, there can be used, for example, solid preparations such as tablets, granules, capsules and the like; and liquid preparations such as solution, fat emulsion, liposome suspension and the like. The present compound, when used in pharmaceutical preparations for oral administration, may also be made in such pharmaceutical preparations by forming on inclusion compound with α-, β- or γ-cyclodextrin, methylated cyclodextrin or the like. As the preparation for intravenous administration, there can be used an aqueous or non-aqueous solution, an emulsion, a suspension, a solid preparation which is used by dissolving in a solvent for injection, right before the use, etc. As the preparation for intrarectal administration, there can be used suppositories; and as the preparation for inatravaginal administration, there can be used preparations such as pessary and the like.

As the adjuvants used for making such pharmaceutical preparations, there can be cited, for example, excipients such as crystalline cellulose, lactose, corn starch, mannitol and the like; lubricants such as magnesium stearate, talc and the like; binders such as hydroxypropyl cellulose, polyvinylpyrrolidone and the like; disintegrators such as carboxymethyl cellulose calcium and the like; fluidity improvers such as light silicic acid anhydride and the like; dissolving agents such as distilled water for injection, physiological saline solution, Ringer's solution and the like; preservatives such as methyl p-oxybenzoate, propyl p-oxybenzoate and the like; emulsifiers such as gum arabic, lecithin and the like; and surfactants such as Tween, Span and the like.

The dose of the present compound can be varied over a wide range depending upon the age, sex and weight of patient, the condition of disease, the judgement of doctor, etc. However, the daily dose for one ordinary adult is 0.1–100 μg, and such a daily dose can be administered in 1–3 to portions as necessary.

Best Mode for Carrying Out the Invention

The present invention is hereinafter described in more detailed by referring to Examples.

In the nomenclature of compound, "nor" in the expression of, for example, "17,18,19,20-tetranor" means that there is no carbon chain at the positions (in the above example, there is no carbon chain at the 17–20 positions).

Production Example 1

4-Thia-5-carbomethoxypentylzinc (II) iodide (1) AIBN (1.93 g, 11.8 mmol) was added to a mixture of methyl thioglycollate (25.0 g, 236 mmol) and allyl alcohol (19.2 ml, 282 mmol). The mixture was stirred at 110° C. for 2 hours. Thereto was added a saturated aqueous sodium chloride solution (100 ml), followed by extraction with ethylacetate (300 ml ). The organic layer was washed with a saturated aqueous sodium chloride solution, dried over magnesium sulfate, and filtered. The filtrate was concentrated to obtain methyl (3-hydroxypropylthio)acetate (38.33 g).

(2) Methyl (3-hydroxypropylthio)acetate (25.68 g) was dissolved in dimethyl chloride (250 ml). Thereto were added, at 0° C., methanesulfonyl chloride (14.5 ml, 187 mmol) and triethylamine (26.2 ml, 188 mmol). The mixture was stirred at room temperature for 30 minutes. Water was added and extraction with dimethyl chloride was conducted. The organic layer was washed with 3N HCl, a saturated aqueous sodium hydrogen carbonate solution and a saturated aqueous sodium chloride solution, dried over anhydrous magnesium sulfate, and filtered. The filtrate was concentrated to obtain methyl (3-methanesulfoxypropylthio)acetate (38.0 g).

(3) Methyl (3-methanesulfoxypropylthio)acetate (57.2 g, 236 mmol) was dissolved in acetone (600 ml). Thereto was added sodium iodide (70.7 g, 472 mmol). The mixture was stirred at room temperature for 3 days. Water was added to the reaction mixture, followed by extraction with ethyl acetate. The organic layer was washed with a saturated aqueous sodium hydrogencarbonate solution and a saturated aqueous sodium chloride solution, dried over anhydrous magnesium sulfate, and filtered. The filtrate was concentrated. The resulting crude product was purified by silica gel column chromatography (developing solvent: ethyl acetate / hexane=1/10) to obtain methyl (3-iodopropylthio)acetate (45.0 g).

$^1$H-NMR (CDCl$_3$, 200 MHz) δ ppm: 2.02–2.17 (m, 2H), 2.75 (t, J=6.9 Hz, 2H), 3.24 (s, 2H), 3.29 (t, J=6.7 Hz, 2H), 3.75 (s, 3H)

(4) To a zinc powder (1.93 g, 29.6 mmol) were added THF (5 ml) and 1,2-dibromoethane (0.05 ml). The mixture was refluxed with heating and stirring. Thereto were added, with stirring at room temperature, trimethylsil chloride (0.10 ml), methyl (iodopropylthio)acetate (4.08 g, 14.8 mmol) and THF (10 ml) in this order. The mixture was stirred with heating, at 40° C. for 2.5 hours to obtain a THF solution of the title compound.

Production Example 2
4-Oxo-5-carbomethoxypentylzinc (II) iodide (1) To sodium hydride (9.6 g, 0.40 mol) was dropwise added trimethylene glycol (144.5 ml, 2.0 mol) at 0° C. The mixture was stirred at room temperature for 3 hours. Thereto was dropwise added, at 0° C., methyl bromoacetate (44.4 ml, 0.40 mol). The mixture was stirred at room temperature for 1.5 hours. The reaction mixture was subjected to silica gel column chromatography (developing solvent: ethyl acetate / methanol=19/1) to remove sodium bromide. After concentration, the concentrate was dissolved in sodium methoxide (2.16 g, 0.04 mol) and methanol (200 ml ). The mixture was stirred at room temperature for 10 minutes, then neutralized with 6N hydrochloric acid, and concentrated. The concentrate was purified by silica gel column chromatography (developing solvent=ethyl acetate / methanol=19/1) to obtain methyl 3-hydroxypropyloxyacetate (36.25 g).

$^1$H-NMR (CDCl$_3$, 200 MHz) δ ppm: 1.17–1.93 (m, 2H), 2.19 (br. s, 1H), 3.70 (t, J=5.5 Hz, 2H), 3.76 (s, 3H), 3.81 (t, J=6.0 Hz, 2H), 4.10 (s, 2H)

(2) Substantially the same procedure as in Production Example 1 (2) to (4) was repeated to produce a THF solution of the title compound.

EXAMPLE 1

(17R)-17,20-Dimethyl-13,14-didehydro-3-oxa-PGE$_1$ methyl ester (compound 1)

(1) In toluene (52 ml) was dissolved (3S,5R)-3-(t-butyldimethylsiloxy)-5-methylnon-1-yne (3.49 g). Thereto was added, at 0° C., n-butyllithium (2.5M, hexane solution, 4.8 ml). The mixture was stirred at the same temperature for 30 minutes. Thereto was added, at 0° C., diethylaiuminum chloride (0.94M, hexane solution, 14.9 ml). The mixture was heated to room temperature and stirred for 30 minutes.

To the mixture was added, at room temperature, (4R)-2-(N,N-diethylamino)methyl-4-(t-butyldimethylsiloxy)cyclopent-2-en-1-one (0.25M, benzene solution, 40 ml). The resulting mixture was stirred for 15 minutes.

The reaction mixture was poured into a mixture of hexane (100 ml), a saturated aqueous ammonium chloride solution (100 ml) and aqueous hydrochloric acid solution(3M, 28 ml), with stirring. The organic layer was separated, washed with a saturated aqueous sodium hydrogencarbonate solution (100 ml), dried and concentrated. The resulting residue was purified by silica gel column chromatography (developing solvent: hexane/ethyl acetate=50/1) to obtain (3R, 4R)-2-methylene-3[(3'S,5'R)-3'-(t-butyldimethylsiloxy)-5'-methylnon-1'-ynyl ]-4-(t-butyldimethylsiloxy)cyclopentan-1-one (3.13 g).

$^1$H-NMR (CDCl$_3$, 300 MHz) δ ppm: 0.03–0.15 (m, 12H), 0.80–0.93 (m, 24H), 1.06–1.80 (m, 9H ), 2.33 (dd, J=7.4 Hz, 17.9 Hz, 1H), 2.71 (dd, J=6.4 Hz, 17.9 Hz, 1H), 3.41–3.56 (m, 1H), 4.20–4.32 (m, 1H), 4.44 (t, J=6.6 Hz, 1H), 5.55 (br. s, 1H), 6.14 (br. s, 1H)

IR (neat): 2920, 2850, 2210, 1730, 1630, 1450, 1360, 1240, 1100, 1080, 820, 760 cm$^{-1}$ (2) To the compound obtained in Production Example 2 (0.88M, tetrahydrofuran solution, 7.10 ml) was added, at −10° C., copper (I) cyanide.lithium dichloride (1.0M, tetrahydrofuran solution, 7.85 ml). The mixture was stirred at the same temperature for 15 minutes. Thereto were added, at −78° C., chlorotrimethylsilane (0.72 ml) and a diethyl ether solution (12.6 ml) of the compound obtained in the above (1) (1.55 g). The mixture was heated to 0° C. in about 2hours, with stirring.

To the reaction mixture was added a saturated aqueous ammonium chloride solution (50 ml), followed by extraction with hexane. The organic layer was washed with a saturated aqueous sodium chloride solution, dried and concentrated. The resulting residue was dissolved in a mixture of diethyl ether (3.2 ml), isopropanol (12.8 ml) and pyridinium p-toluenesulfonate (40 mg). The solution was stirred at room temperature for 15 hours.

To the reaction mixture were added hexane (30 ml) and a saturated aqueous sodium hydrogencarbonate solution (50 ml), and extraction was conducted. The organic layer was dried and concentrated. The resulting residue was subjected to silica gel column chromatography (developing solvent: hexane/ethyl acetate=9/1) to obtain (17R)-3-oxa-17,20-dimethyl-13,14-didehydro-PGE$_1$ methyl ester 11,15-bis(t-butyldimethylsilyl ether) (1.17 g).

$^1$H-NMR (CDCl$_3$, 200 MHz) δ ppm: 0.09 (s, 6H), 0.11 (s, 3H), 0.12 (s, 3H), 0.86–0.94 (m, 6H), 0.89 (s, 18H), 1.18–1.85 (m, 15H), 2.04–2.27 (m, 1H), 2.17 (dd, J=6.9 Hz, 17.7 Hz, 1H), 2.58–2.76 (m, 2H), 3.52 (t, J=6.5 Hz, 2H), 3.76 (s, 3H), 4.07 (s, 2H), 4.22–4.34 (m, 1H), 4.36–4.45 (m, 1H)

IR (neat): 2955, 2930, 2858, 2234, 1747, 1463, 1439, 1378, 1362, 1254, 1208, 1141, 1094, 1006, 940, 839, 779, 670 cm$^{-1}$ (3) The compound obtained in the above (2) (1.06 g, 1.70 mmol) was dissolved in acetonitrile (56.5 ml). Thereto was added 40% hydrofluoric acid (12.8 ml) at 0° C. The mixture was stirred for 15 hours with heating to room temperature. The reaction mixture was poured into ethyl acetate (100 ml) and a saturated aqueous sodium hydrogencarbonate solution (300 ml). The aqueous layer was extracted with ethyl acetate (100 ml). The resulting organic layer was washed with a saturated aqeuous sodium hydrogencarbonate solution and a saturated aqueous sodium chloride solution, dried and concentrated. The resulting residue was purified by silica gel column chromatography (developing solvent: hexane / ethyl acetate=9/11) to obtain the title compound (440 mg).

$^1$H-NMR (CDCl$_3$, 300 MHz) δ ppm: 0.87–0.94 (m, 6H), 1.08–1.88 (m, 15H), 2.20–2.31 (m, 1H ), 2.24 (dd, J=9.0 Hz, 18.5 Hz, 1H), 2.32 (d, J=5.3 Hz, 1H), 2.48–2.55 (m, 1H), 2.64–2.71 (m, 1H), 2.75 (ddd, J=1.3 Hz, 7.2 Hz, 18.5 Hz, 1H), 3.51–3.57 (m, 2H), 3.75 (s, 3H), 4.08 (s, 2H), 4.29–4.38 (m, 1H), 4.43–4.50 (m, 1H)

IR (neat): 3431, 2954, 2930, 2871, 2236, 1746, 1440, 1379, 1285, 1217, 1141, 1072 cm$^{-1}$

EXAMPLE 2

(17R)-17,20-Dimethyl-13,14-didehydro-3-oxa-PGE$_1$ (compound 2)

PLE (Sigma Co., 210 units aqueous ammonium sulfate solution, 190 µl) was dissolved in a phosphate buffer (pH=8, 17 ml) and acetone (9.6 ml). Thereto was added the compound obtained in Example 1 (380 mg). The mixture was stirred at room temperature for 15 hours and then subjected to salting out with sodium chloride and extraction with ethyl acetate. The organic layer was washed with a saturated aqueous sodium chloride solution, dried over anhydrous magnesium sulfate, and concentrated. The resulting crude product was purified by silica gel column chromarography (developing solvent: ethyl acetate) to obtain the title compound (330 mg).

$^1$H-NMR (CDCl$_3$, 300 MHz) δ ppm: 0.87–0.94 (m, 6H), 1.11–1.89 (m, 15H), 2.24–2.30 (m, 1H), 2.25 (dd, J=9.1 Hz, 1H), 2.65–2.79 (m, 1H), 2.76 (ddd, J=1.2 Hz, 7.3 Hz, 18.5 Hz, 1H), 3.53–3.59 (m, 2H), 4.09 (s, 2H), 4.29–4.37 (m, 1H), 4.45–4.50 (m, 1H)

IR (neat): 3402, 2930, 2871, 2238, 1742, 1461, 1377, 1240, 1136, 1050, 677 cm$^{-1}$

EXAMPLE 3

(17S)-20-Isopropylidene-17-methyl-13, 14-didehydro-3-thia-PGE$_1$ methyl ester (compound 3)

(1) (3R,4R)-2-Methylene-3-[(3'S,5'S)-3'-(t-butyldimethylsiloxy)-5',9'-dimethyldec-8'-en-1'-ynyl]-4-t-butyldimethylsiloxy)cyclopentan-1-one was obtained substantially in the same manner as in Example 1(1), using (3S,5S)-3-(t-butyldimethylsiloxy)-5,9-dimethyldec-8-en-1-yne in place of the (3S,5R)-3-(t-butyldimethylsiloxy)-5-methylnon-1-yne used in Example 1 (1).

$^1$H-NMR (CDCl$_3$, 200 MHz) δ ppm: 0.10 (s, 6H), 0.11 (s, 3H), 0.13 (s, 3H), 0.78–0.96 (m, 3H ), 0.90 (s, 18H ), 1.07–2.08 (m, 7H), 1.60 (s, 3H), 1.67 (d, J=0.9 Hz, 3H), 2.32 (dd, J=7.4 Hz, 18.0 Hz, 1H), 2.71 (dd, J=6.4 Hz, 18.0 Hz, 1H), 3.48–3.57 (m, 1H), 4.21–4.34 (m, 1H), 4.38–4.51 (m, 1H), 5.03–5.15 (m, 1H), (m, 1H), 5.55 (dd, J=0.7 Hz, 2.8 Hz, 1H), 6.14 (dd, J=0.7 Hz, 3.1 Hz, 1H)

(2) By using the compound obtained in the above (1) and conducting substantially the same procedure as in Example 1 (2), there was obtained (17S)-20-isopropylidene-17-methyl-13,14-didehydro-3-thiac-PGE$_1$ methyl ester 11,15-(t-butyldimethylsilyl ether).

$^1$H-NMR (CDCl$_3$, 200 MHz) δ ppm: 0.09 (s, 3H), 0.10 (s, 3H), 0.11 (s, 3H), 0.13 (s, 3H), 0.84–0.92 (m, 3H), 0.89 (s, 9H), 0.90 (s, 9H), 1.05–2.08 (m, 13H), 1.60 (s, 3H), 1.68 (d, J=0.9 Hz, 3H), 2.10–2.24 (m, 1H), 2.17 (dd, J=6.5 Hz, 18.2 Hz, 1H), 2.57–2.74 (m, 4H), 3.21 (s, 2H), 3.74 (s, 3H), 4.23–4.34 (m, 1H), 4.36–4.48 (m, 1H), 5.03–5.14 (m, 1H)

IR (neat): 2954, 2930, 2857, 2235, 1747, 1463, 1437, 1377, 1362, 1279, 1255, 1131, 1099, 1074, 1007, 939, 838, 778, 670 cm$^{-1}$ (3) By using the compound obtained in the above (2) and conducting substantially the same procedure as in Example 1 (3), the title compound was obtained.

$^1$H-NMR (CDCl$_3$, 300 MHz) δ ppm: 0.94 (d, J=6.4 Hz, 3H), 1.14–1.28 (m, 13H), 1.61 (s, 3H), 1.68 (d, J=1.1 Hz, 3H), 2.13 (d, J=5.6 Hz, 1H), 2.19–2.28 (m, 1H), 2.24 (dd, J=9.0 Hz, 18.5 Hz, 1H), 2.50 (d, J=3.4 Hz, 1H), 2.61–2.69 (m, 3H), 2.76 (ddd, J=1.3 Hz, 7.3 Hz, 18.5 Hz, 1H), 3.22 (s, 2H), 3.74 (s, 3H), 4.28–4.38 (m, 1H), 4.44–4.52 (m, 1H) 5.06–5.14 (m, 1H)

IR (neat): 3401, 2927, 2858, 2236, 1742, 1438, 1378, 1284, 1153, 1088, 1012 cm$^{-1}$

EXAMPLE 4

(17S)-20-Isopropylidene-17-methyl-13,14-didehydro-3-thia-PGE$_1$ (compound 4)

By using the compound obtained in Example 3 and conducting substantially the same procedure as in Example 2, the title compound was obtained.

$^1$H-NMR (CDCl$_3$, 300 MHz ) δ ppm: 0.94 (d, J=6.3 Hz, 3H), 1.13–2.06 (m, 19H), 2.22–2.31 (m, 1H), 2.25 (dd, J=9.0 Hz, 18.5 Hz, 1H), 2.63–2.73 (m, 3H), 2.76 (ddd, J=1.3 Hz, 7.3 Hz, 18.5 Hz, 1H), 3.23 (s, 2H), 4.27–4.39 (m, 1H), 4.48–4.56 (m, 1H), 5.05–5.14 (m, 1H)

IR (neat): 3392, 2927, 2857, 2238, 1734, 1455, 1379, 1288, 1157, 1088 cm$^{-1}$

EXAMPLE 5

(17R)-20-Isopropylidene-17-methyl-13, 14-didehydro-3-oxa-PGE$_1$methyl ester (compound 5)

(1) (3R,4R)-2-Methylene-3-[(3'S,5'R)-3'-(t-butyldimethylsiloxy)-5',9'-dimethyldec-8'-en-1'-ynyl]-4-(t-butydimethysiloxy)cycopentan-1-one was obtained substantially in the same manner as in Example 1 (1), using (3S,5R)-3-(t-butyldimethysiloxy)-5,9-dimethyldea-8-en-1-yne in place of the (3S, 5R)-3-(t-butyldimethylsiloxy)-5-methylnon-1-yne used in Example 1 (1).

$^1$H-NMR (CDCl$_3$, 200 MHz ) δ ppm: 0.10 (S, 6H), 0.11 (s, 3H), 0.14 (s, 3H), 0.75–1.02 (m, 3H), 0.89 (s, 9H), 0.90 (s, 9H), 1.07–2.08 (m, 7H), 1.60 (s, 3H), 1.68 (s, 3H), 2.32 (dd, J=7.3 Hz, 17.9 Hz, 1H), 2.72 (dd, J=6.5 Hz, 17.9 Hz, 1H), 3.48–3.57 (m, 1H), 4.21–4.34 (m, 1H ), 4.36–4.51 (m, 1H), 5.03–5.15 (m, 1H), 5.55 (dd, J=0.6 Hz, 2.6 Hz, 1H), 6.14 (dd, J=0.6 Hz, 3.0 Hz, 1H )

(2) By using the compound obtained in the above (1) and conducting substantially the same procedure as in Example 1 (2), there was obtained (17R)-20-isopropylidene-17-methyl-13,14-didehydro-3-oxa-pGE$_1$ methyl ester 11,15-(t-butyldimethylsilyl ether).

$^1$H-NMR (CDCl$_3$, 200 MHz) δ ppm: 0.09 (s, 6H), 0.11 (s, 3H), 0.13 (s, 3H), 0.87–0.94 (m, 3H), 0.89 (s, 18H), 1.08–2.05 (m, 13H), 1.60 (s, 3H), 1.68 (d, J=1.0 Hz, 3H), 2.10–2.21 (m, 2H), 2.60–2.73 (m, 2H), 3.52 (t, J=6.4 Hz, 2H), 3.75 (s, 3H), 4.07 (s, 2H), 4.22–4.34 (m, 1H), 4.38–4.51 (m, 1H), 5.07–5.13 (m, 1H)

IR (neat): 2954, 2930, 2858, 2235, 1748, 1473, 1463, 1439, 1377, 1362, 1253, 1207, 1141, 1100, 1006, 940, 839, 810, 779, 670 cm$^{-1}$ 5 (3) By using the compound obtained in the above (2) and conducting substantially the same procedure as in Example 1 (3), the title compound was obtained.

$^1$H-NMR (CDCl$_3$, 300 MHz) δ ppm: 0.95 (d, J=6.6 Hz, 3H), 1.13–2.07 (m, 13H), 1.60 (s, 3H), 1.68 (s, 3H), 2.20–2.31 (m, 1H), 2.24 (dd, J=8.9 Hz, 18.5 Hz, 1H), 2.30 (d, J=5.7 Hz, 1H), 2.44 (d, J=3.4 Hz, 1H), 2.64–2.70 (m, 1H), 2.75 (ddd, J=1.2 Hz, 7.2 Hz, 18.5 Hz, 1H), 3.52–3.56 (m, 2H), 3.75 (s, 3H), 4.08 (s, 2H), 4.31–4.35 (m, 1H), 4.45–4.48 (m, 1H), 5.07–5.12 (m, 1H)

IR (neat): 3430, 2928, 2236, 1746, 1440, 1378, 1285, 1217, 1141, 1082 cm$^{-1}$

EXAMPLE 6

(17R)-20-Isopropylidene-17-methyl-13, 14-didehydro-3-oxa-PGE$_1$ (compound 6)

By using the compound obtained in Example 5 and conducting substantially the same procedure as in Example 2, the title compound was obtained.

$^1$H-NMR (CDCl$_3$, 300 MHz) δ ppm: 0.94 (d, J=6.6 Hz, 3H), 1.15–2.06 (m, 13H), 1.60 (s, 3H), 1.68 (s, 3H), 2.20–2.29 (m, 1H), 2.25 (dd, J=9.1 Hz, 18.5 Hz, 1H), 2.64–2.80 (m, 1H), 2.76 (ddd, J=1.2 Hz, 7.3 Hz, 18.5 Hz, 1H), 3.56–3.60 (m, 2H), 4.09 (s, 2H), 4.29–4.37 (m, 1H), 4.46–4.51 (m, 1H), 5.07–5.11 (m, 1H)

IR (neat): 3402, 2929, 2237, 1742, 1446, 1376, 1286, 1148, 1087, 1021, 646 cm$^{-1}$

We claim:

1. A prostaglandin E$_1$ analogue represented by formula

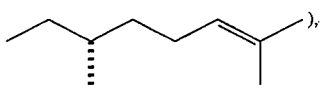

(wherein R$^1$ represents hydrogen atom or a C$_{1-C6}$ alkyl group; and X is an oxygen atom and R$^2$ represents

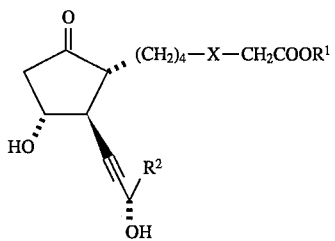

or

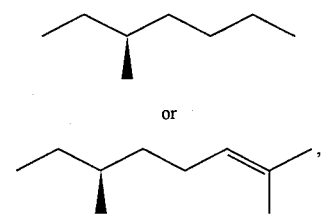

or X is a sulfur atom and R$^2$ represents

and a salt thereof.

2. A compound set forth in claim 1, wherein R$^1$ is a hydrogen atom or a C$_1$–C$_4$ alkyl group.

3. A method for treatment of thrombotic diseases in mammals, which comprises administering, to a mammal, an effective amount of a compound of formula (I) set forth in claim 1 or a pharmaceutically acceptable salt thereof.

4. A pharmaceutical composition comprising:

(1) a prostaglandin E$_1$ analogue represented by formula

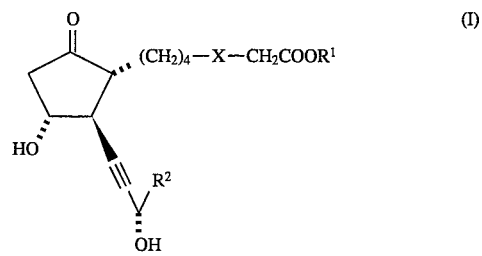

(wherein R$^1$ represents hydrogen atom or a C$_1$–C$_6$ alkyl group; and X is an oxygen atom and R$^2$ represents

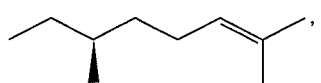

or

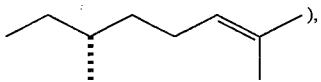

or x is a sulfur atom and R$^2$ represents

or a salt thereof; and (2) a pharmaceutically acceptable adjuvant.

* * * * *

UNITED STATES PATENT AND TRADEMARK OFFICE
CERTIFICATE OF CORRECTION

PATENT NO. : 5,583,158            Page 1 of 4
DATED : December 10, 1996
INVENTOR(S) : SATO et al It is certified that error appears in the above-indentified patent and that said Letters Patent is hereby corrected as shown below:

Col. 1, line 9, "prosta-glandin" should read --prostaglandin--;

line 21, delete "inpractical" insert --in practical--; and line 38, delete "then" insert --than--.

Col. 2, line 1, "prosta-glandin" should read --prostaglandin--;

line 13, delete "wherein" and insert --(wherein--;

line 39, delete "(T)" and insert --(I)--; and line 43, after "the" insert --like;--.

Col. 5, line 23, "tetrahydropyronyl" should read "tetrahydropyranyl";

line 24, "rahydrofuronyl" should read --rahydrofuranyl--;

line 35, "tetrahydrofuron" should read

UNITED STATES PATENT AND TRADEMARK OFFICE
CERTIFICATE OF CORRECTION

PATENT NO. : 5,583,158           Page 2 of 4
DATED      : December 10, 1996
INVENTOR(S): SATO et al It is certified that error appears in the above-indentified patent and that said Letters Patent is hereby corrected as shown below:

--tetrahydrofuran--.

Col. 6, line 15, "wherein" should read --(wherein--;

line 25, "300" should read --30-- and "In" should read --It--;

line 27, "tetrahydrofuron" should read --tetrahydrofuran--;

line 36, "tetrahydrofuron" should read --tetrahydrofuran--.

Col. 7, line 29, delete "a";

line 34, delete "a"; and line 64, after "wherein" insert --$R^1$--.

UNITED STATES PATENT AND TRADEMARK OFFICE
CERTIFICATE OF CORRECTION

PATENT NO. : 5,583,158   Page 3 of 4
DATED : December 10, 1996
INVENTOR(S) : SATO et al It is certified that error appears in the above-indentified patent and that said Letters Patent is hereby corrected as shown below:

Col. 8, line 21, "pan areas" should read --pancreas--;

line 39, delete "to", second instance; and line 64, delete "to".

Col. 9, line 6, "aggregatian" should read --aggregation--.

Col. 10, line 28, delete "on" insert --an--; and line 59, delete "detailed" insert --detail--.

Col. 11, line 40, "trimethylsil" should read --trimethylsilyl--.

Col. 12, line 8, "diethylaiuminum" should read --diethylaluminum--; and line 17, after "and" insert --an--.

UNITED STATES PATENT AND TRADEMARK OFFICE
CERTIFICATE OF CORRECTION

PATENT NO. : 5,583,158
DATED : December 10, 1996
INVENTOR(S) : SATO et al

It is certified that error appears in the above-indentified patent and that said Letters Patent is hereby corrected as shown below:

Col. 13, line 39, Before "1H" insert --18.5 Hz--;

line 61, delete "(m, 1H)", second instance; and line 66, "thiac" should read --thia--.

Col. 14, line 44, "dimethyldea" should read --dimethyldec--; and line 57, "pGE$_1$" should read --PGE$_1$--.

Col. 15, line 1, delete "5";

line 40, "C$_{1-C6}$" should read --C$_1$-C$_6$--.

Col. 16, line 15, "pharmaceutially" should read --pharmaceutically--.

Signed and Sealed this

Ninth Day of December, 1997

BRUCE LEHMAN

Attest:

Attesting Officer

Commissioner of Patents and Trademarks